(12) United States Patent
Berger et al.

(10) Patent No.: US 7,459,170 B2
(45) Date of Patent: Dec. 2, 2008

(54) BONE REPLACEMENT MATERIAL WITH ORTHOPHOSPHATE

(75) Inventors: Georg Berger, Zepernick (DE); Andrea Spitzer, Berlin (DE); Christian Jäger, Berlin (DE); Jutta Pauli, Berlin (DE); Renate Gildenhaar, Berlin (DE)

(73) Assignee: BAM Bundesanstalt fuer Materialforschung und-pruefung, Berlin (DE)

( * ) Notice: Subject to any disclaimer, the term of this patent is extended or adjusted under 35 U.S.C. 154(b) by 922 days.

(21) Appl. No.: 10/689,217

(22) Filed: Oct. 20, 2003

(65) Prior Publication Data

US 2004/0175430 A1    Sep. 9, 2004

(30) Foreign Application Priority Data

Oct. 21, 2002    (DE)    ................................. 102 49 626

(51) Int. Cl.
A61F 2/28    (2006.01)
(52) U.S. Cl. ....................................... 424/426
(58) Field of Classification Search ........................ None
See application file for complete search history.

(56) References Cited

U.S. PATENT DOCUMENTS

| | | | | |
|---|---|---|---|---|
| 3,922,155 A | * | 11/1975 | Broemer et al. | ............... 65/33.3 |
| 4,239,113 A | * | 12/1980 | Gross et al. | ................... 206/568 |
| 6,002,065 A | * | 12/1999 | Constantz et al. | ........... 423/308 |
| 6,117,456 A | | 9/2000 | Lee et al. | |
| 7,223,420 B2 | * | 5/2007 | Berger et al. | ................. 424/489 |

FOREIGN PATENT DOCUMENTS

| | | | |
|---|---|---|---|
| DE | 19744809 C1 | * | 7/1999 |
| EP | 0 237 043 B1 | | 6/1992 |
| EP | 0 541 546 B1 | | 10/1994 |
| WO | 91/07357 | | 5/1991 |

OTHER PUBLICATIONS

Derwent-ACC-No. 1999-348171 Abstracting DE 19744809C1 Jul. 1, 1999.*

* cited by examiner

Primary Examiner—Carlos Azpuru
(74) Attorney, Agent, or Firm—Akerman Senterfitt; Gregory A. Nelson; Gregory M. Lefkowitz

(57) ABSTRACT

The present invention relates to a material with orthophosphate and having a high solubility which can be used as a bioactive bone replacement material and as a substrate material in biotechnology. According to $^{31}$P-NMR measurements, the new material comprises $Q_0$-groups of orthophosphate and $Q_1$-groups of diphosphate, the orthophosphates or $Q_0$-groups making up 65 to 99.9% by weight relative to the total phosphorus content of the finished material and the diphosphates or $Q_1$-groups making up 0.1 to 35% by weight relative to the total phosphorus content of the finished material, and wherein according to X-ray diffractometric measurements and relative to the total weight of the finished material, 35 to 99.9% by weight of a main crystal phase consisting of $Ca_{10}Na(PO_4)_7$, $Ca_{10}K(PO_4)_7$, mixtures thereof or mixed crystals according to the general formula $Ca_{10}K_xNa_{1-x}(PO_4)_7$, where x=0 to 1, is contained in the bone replacement material and 0.1 to 25% by weight of a substance selected from the group consisting of $Na_2CaP_2O_7$, $K_2CaP_2O_7$, $Ca_2P_2O_7$ and mixtures thereof is contained as a secondary crystal phase, and the X-ray amorphous phases contained besides the main crystal phase jointly make up 0.1 to 65% by weight.

18 Claims, 2 Drawing Sheets $^{31}$P-MAS-NMR spectra of the compositions according to codes 50-25-25 and 30-50-20

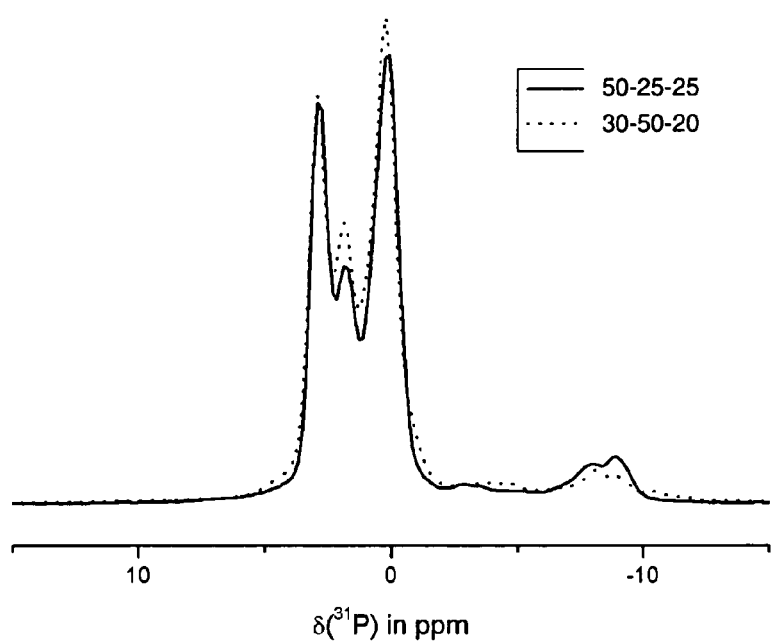
Fig. 1: $^{31}$P-MAS-NMR spectra of the compositions according to codes 50-25-25 and 30-50-20

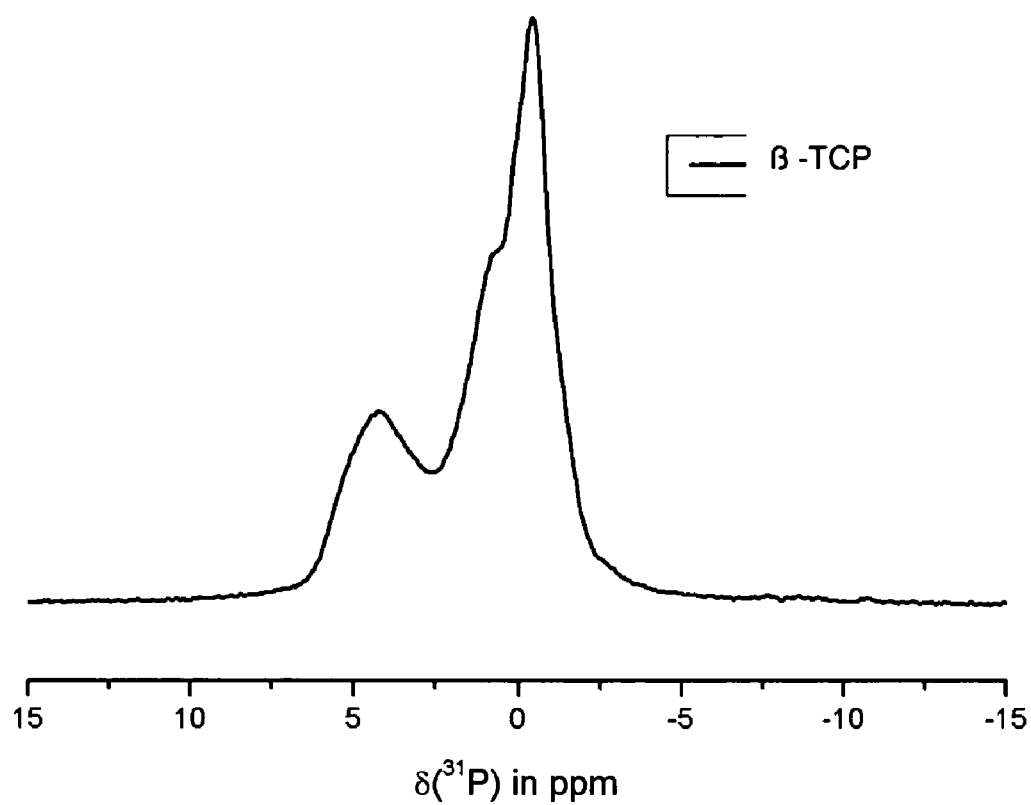
Fig. 2: $^{31}$P-MAS-NMR spectrum of β-TCP

BONE REPLACEMENT MATERIAL WITH ORTHOPHOSPHATE

TECHNICAL FIELD OF THE INVENTION

The present invention relates to a material comprising orthophosphate and having a high solubility which can be used both as a bioactive bone replacement material, e.g. in the form of a spongiosa-like material, a coating applied onto metallic prosthesis sticks by thermal spraying or by rf sputtering, and as a substrate material in biotechnology, especially in tissue engineering, e.g. in the form of a ceramic sheet or of a compact or porous, i.e. spongiosa-like, scaffold-like, moulded body. The invention also relates to a manufacturing method.

BACKGROUND OF THE INVENTION

In principle, inorganic materials which are easily resorbed are known. Materials which are specifically used as bioactive bone replacement materials and dissolve quickly have also been described in the relevant literature. For example, there have been numerous publications dedicated to the successful clinical use of ceramic materials the main crystal phases of which are alpha- or beta-tricalcium phosphate (TCP). In addition, there have been comparative analyses of these two TCP phases using animal tests. It is known from EP 237043 that granulated materials made of alpha-TCP contain dicalcium phosphate on their surface, whose solubility was higher than that of the pure alpha-PCT core material, especially in the initial phase following an implantation.

The chemical solubility of the aforesaid granulated materials was surpassed by other bioactive materials based on calcium phosphates which in addition contain oxides of potassium, sodium, magnesium and/or silicon (EP 541564 B1) and the glassy-crystalline material of which is based on the following main crystal phases: Phase X, rhenanite, phase according to Ando (Phase A) and/or mixed crystals derived from the aforesaid phases in between these crystal phases.

SUMMARY OF THE INVENTION

The object of the invention is to provide a new material comprising orthophosphate which comprises further phosphates and enables a substantially direct joining of bones without connective tissue and/or the ex vivo cultivation of bone cells, and which dissolves in contact with bone tissue, and which at the same time has solubilities which are adjustable in a more precise manner and, in the case of composite materials, coefficients of expansion adapted to certain metals. Another object of the invention is to provide a method for manufacturing the aforesaid material.

DETAILED DESCRIPTION OF THE INVENTION

According to the invention, the bone replacement material comprises:
a) according to $^{31}$P-NMR measurements, $Q_0$-groups of orthophosphate and $Q_1$-groups of diphosphate, the orthophosphates or $Q_0$-groups making up 65 to 99.9% by weight relative to the total phosphorus content of the finished material and the diphosphates or $Q_1$-groups making up 0.1 to 35% by weight relative to the total phosphorus content of the finished material, and
b) according to X-ray diffractometric measurements and relative to the total weight of the finished material, 35 to 99.9% by weight of a main crystal phase consisting of $Ca_{10}Na(PO_4)_7$, $Ca_{10}K(PO_4)_7$, mixtures thereof or mixed crystals according to the general formula $Ca_{10}K_xNa_{1-x}(PO_4)_7$, where x=0 to 1, and 0.1 to 25% by weight of a substance selected from the group consisting of $Na_2CaP_2O_7$, $K_2CaP_2O_7$, $Ca_2P_2O_7$ and mixtures thereof as a secondary crystal phase, and
c) X-ray amorphous phases contained besides the main crystal phase which jointly make up 0.1 to 65% by weight relative to the total weight of the finished material.

Preferably, x ranges between 0.1 and 1, particularly 0.2 and 1.

In addition, the secondary crystal phase or the amorphous phase preferably contain one or more substances from the group consisting of $\beta\text{-}Ca_3(PO_4)_2$, $Ca_2K_{1-x}Na_{1+x}(PO_4)_2$ (x=0.1-1), $CaNaPO_4$, $NaPO_3$, $KPO_3$ and mixed crystals thereof, the chain phosphates $NaPO_3$ and $KPO_3$ being detectable as $Q_2$-groups according to $^{31}$P-NMR measurements and the orthophosphates being detectable as $Q_0$-groups according to $^{31}$P-NMR measurements.

Further the secondary phase may contain a silicate phase in an amount ranging up to 6% by weight, corresponding to the $SiO_2$ content.

In mixed crystals contained in the aforesaid main crystal phase and in the constituents of the secondary crystal phase, the element Ca may be replaced by Mg in an amount ranging up to 10% by weight relative to the weight of the finished material.

The orthophosphate phase represented by $Q_0$-groups preferably makes up 40 to 95% by weight, particularly 50 to 90% by weight.

The diphosphate phase represented by $Q_1$-groups preferably makes up 1 to 22% by weight, particularly 5 to 8% by weight.

The composition of the material according to the invention which is based on CaO, $P_2O_5$, $Na_2O$, $K_2O$ and optionally MgO and $SiO_2$ and which is to be regarded as X-ray amorphous-crystalline ranges between (in % by weight):
35 and 55 $P_2O_5$; 30 and 50 CaO;
1 and 12 $Na_2O$; 0.5 and 15 $K_2O$;
0 and 5 MgO, preferably 0.1-5 MgO;
0 and 5 $SiO_2$; MgO or $SiO_2$ or a mixture thereof making up at least 1% by weight.

The composition comprises the aforesaid phases as main crystal phases and one or more constituents from the group consisting of $Na_2CaP_2O_7$, $K_2CaP_2O_7$, $Ca_2P_2O_7$, $\beta\text{-}Ca_3(PO_4)_2$, $Ca_2K_{1-x}Na_{1+x}(PO_4)_2$, where x=0.1-0.9, $CaNaPO_4$, $NaPO_3$ and $KPO_3$ as crystalline secondary constituents as well as an X-ray amorphous phase.

A preferred material contains the following constituents (in % by weight): 43 to 55 $P_2O_5$, 32 to 48 CaO, 1.5 to 11 $Na_2O$, 1.5 to 12 $K_2O$, 0.5 to 2 MgO, 0.0 to 2 $SiO_2$. A special preferred embodiment contains 44 to 54 $P_2O_5$, 34 to 48 CaO, 1.5 to 10.5 $Na_2O$, 1 to 11 $K_2O$, 1.5 to 3 MgO, 0.1 to 4 $SiO_2$.

In general, the term "X-ray amorphous"0 material used herein cannot be clearly defined. "X-ray amorphous" as used herein refers to a material whose structure cannot be determined using standard XRD (X-ray diffractometry) and which can therefore be called X-ray amorphous. The undetectable areas can be very small organized areas (micro-crystalline) as well as statistically unorganized areas. Unlike XRD, the $^{31}$P-NMR results can be used to detect the existence of any crystalline phase. Therefore quantitative estimates based on NMR and XRD results can be rather different. This phenomenon seems to be particularly true of the diphosphate and chain phosphate contents; as a rule, $^{31}$P-NMR measurements yield considerably higher contents than XRD and in some cases no contents at all of crystalline parts of the last mentioned phosphates are found using XRD. This impressively shows why $^{31}$P-NMR measurements are an essential prerequisite for characterizing and finally manufacturing the materials according to the invention. XRD measuring with PW 1710, Philipps, NL (CuK radiation).

Both crystalline and X-ray amorphous phases can therefore be provided in a thoroughly mixed state. It is of no importance for the present invention whether one phase is located adjacent to the other or one phase encloses the other. The term "main crystal phase" as used herein refers to a crystalline phase which is detected using X-ray diffraction and is contained in at least twice the amount of a secondary phase, concentrations of 25% and below, preferably below 15% by weight, being referred to as secondary phases.

Surprisingly, it has been found, that a high solubility can be achieved by means of the main phases $Ca_{10}Na(PO_4)_7$, $Ca_{10}K(PO_4)_7$ and K-Na ratios in between according to the aforesaid formulas (orthophosphates) and by the secondary phases $Na_2CaP_2O_7$, $K_2CaP_2O_7$ and $Ca_2P_2O_7$ (diphosphates), i.e. that relatively small alkali contents bring about the same effect as described in the relevant literature for compositions containing solely $Ca_2KNa(PO_4)_2$. In addition, an increasing substitution of potassium by sodium does not lead to an abrupt phase transition as in the case of $Ca_2KNa(PO_4)_2$, which inevitably changes into $Ca_5Na_2(PO_4)_4$, but the only effect is a change in the amounts of the $Ca_{10}Na(PO_4)_7$ and $Ca_{10}K(PO_4)_7$ phases and/or the mixed crystals according to the general formula $Ca_{10}K_xNa_{1-x}(PO_4)_7$, where x=0-1, which may have formed in between these substances, without any abrupt phase transition.

Preferably, x ranges between 0.1 and 1, particularly 0.2 and 1.

Further, it has surprisingly been found that the main crystal phases $Ca_{10}Na(PO_4)_7$ and $Ca_{10}K(PO_4)_7$ and K-Na ratios in between can be unequivocally characterized by means of $^{31}$P-NMR measurements and that in contrast to the X-ray diffractometric method used so far [XRD files: PDF-2 (1996) 450339 and 450138; Zh.Neoorg.Khim., 33(1988)73, including the instructions for preparing $Ca_{10}Na(PO_4)_7$ and $Ca_{10}K(PO_4)_7$ contained therein] no confusion with or problems regarding the identification of the beta-TCP phase can occur. The presence of the main crystal phases according to the invention also accounts for the much higher solubility of these glassy-crystalline materials compared to alpha- and/or beta-TCP.

The $^{31}$P-NMR measurements, which were carried out using a superconductive Fourier NMR spectrometer known as Avance DMX400 WB and manufactured by Bruker BioSpin GmbH (Germany), also showed that the material preferably consists of 65 to 99.9 orthophosphate of calcium and in some cases orthophosphate of sodium, potassium and magnesium, wherein the aforesaid orthophosphate content is determined using $^{31}$P-NMR measurements ($Q_0$-groups) and refers to crystalline and/or X-ray amorphous material in its entirety, 0.1 to 35% diphosphate of calcium and in some cases diphosphate of sodium, potassium and magnesium, wherein the aforesaid diphosphate content is determined using $^{31}$P-NMR measurements ($Q_1$-groups) and refers to crystalline and/or amorphous material in its entirety, 0 to 15% chain phosphate of sodium and/or potassium, wherein the aforesaid chain phosphate content is determined using $^{31}$P-NMR measurements ($Q_2$-groups) and refers particularly to X-ray amorphous and, as the case may be, micro-crystalline material in its entirety. In addition, 0 to 10% of a silicate phase may be contained, depending upon the amount of $SiO_2$ added.

Further, it has surprisingly been found that the desired effect, i.e. a considerably improved solubility, is brought about by the presence of diphosphates and/or chain phosphates, preferably diphosphates, as will be demonstrated in Example 4. In contrast to the alpha-TCP having an outer layer of dicalcium phosphate, which is mentioned in the section describing the state of the art, all diphosphates of the material according to the invention are "thoroughly mixed" with the other phase constituents, i.e. the phase does not have a layered structure, which brings about a high solubility or even enables the complete disappearance or biodegradation of the material.

The diphosphate contents result from a comparatively high phosphate content relative to the other constituents. The aforesaid phosphate content could also be the reason why the compositions according to the invention melt very easily yielding a rather fluid melt compared to known resorbable materials.

Further, it has surprisingly been found that due to the presence of diphosphates the ion discharge behaviour of the material (the glassy-crystalline material), which in the beginning shows a strong alkaline reaction, changes more pronouncedly towards physiological pH values (7.4) than that of materials not containing diphosphate, provided the material was stored in deionized water. Due to this shift in pH values, the material is also of interest to biotechnology, in particular to tissue engineering.

The aforesaid feature can be enhanced by boiling the (compact or open-pore) moulded bodies in deionized water (37-90° C.) and optionally at a pressure ranging up to 10 bars thus leaching their surface so that the material or moulded body treated in this way has considerably lower pH values once the treatment is finished. This phenomenon could be put down to a reduction of the alkaline Ions in the area near the surface of the material. Such an embodiment of the invention is preferred.

Another feature of the material according to the invention consists in that its solubility can be adjusted within relatively wide ranges, depending upon the selected composition; specifically, the total solubility can range between 60 and 250 μg/mg relative to the starting material if the test is carried out in 0.2M TRIS-HCl buffer solution at pH=7.4, T=37° C. using a grain size fraction of 315-400 μm, the duration of the test being 120 h and the ratio of weighed-in sample to buffer solution being 50 mg to 40 ml.

Another feature of the material consists in that it can be ground more finely than materials containing solely $Ca_xKNa(PO_4)_2$ as main crystal phase under the same grinding conditions (Pulverizette 5 manufactured by Frisch GmbH, $ZrO_2$ grinding bowl) [described in: Biomaterials 16 (1995)1241-1248]. The aforesaid feature, which may be due to a high content of X-ray amorphous substances, is of particular importance if the material is to be processed into spongiosa-like bodies.

According to the invention, the material is manufactured by combining the substances suitable for preparing the mixture to be melted, their concentrations being in the range of 35-55% by weight CaO, 30-50% by weight $P_2O_5$, 1-12% by weight $Na_2O$, 0.5-15% by weight $K_2O$ and 0-5% by weight MgO and optionally up to 5% by weight $SiO_2$, MgO or $SiO_2$ or a mixture thereof making up at least 1% by weight, and melting the mixture at between 1,550 and 1,650° C. in a suitable crucible material, e.g. consisting of a Pt/Rh alloy, using multistage thermal treatment programmes (holding stages in the range between 200 and 1,500° C., namely 1-2 h at 350-450° C., 750-850° C. and 950-1,050° C., e.g. 1 h at 400, 800 and 1,000° C. respectively or e.g. 1 h at 800° C. and 1 h at 950° C.). The melt may be held at the melting temperature for between 20 and 60 min. The melt is then poured and once the mass has solidified it is cooled down to room temperature in air (spontaneous cooling) or in a cooling furnace using a temperature-controlled cooling process, e.g. at a rate of 1 to 20 degrees/min, depending upon its intended use. A spontaneous crystallization process takes place while the melt cools down. The mixture to be melted may comprise oxides, carbonates, hydrogen phosphates and/or orthophosphoric acid. The $^{31}$P-NMR measurements yield different spectra allowing conclusions as to the raw materials used or indicating small amounts of iron oxides or manganese oxides contained therein.

Preferred melting temperatures range between 1,590 and 1,650° C.

Once the material has cooled down, it is e.g. ground, mixed with commonly used sintering aids and isostatically pressed into moulded bodies in order to obtain a densely fired ceramic body after sintering.

Alternatively, the material manufactured according to the invention can e.g. be ground, mixed with commonly used sintering aids and processed into a slurry which is then applied onto a polyurethane sponge and sintered in several sintering stages at such high temperatures that the polyurethane sponge and the sintering aids are burnt completely and a spongiosa-like body is obtained the main crystalline constituents of which are $Ca_{10}Na(PO_4)_7$, $Ca_{10}K(PO_4)_7$ and in some cases mixed crystals in between these two phases as well as $Na_2CaP_2O_7$, $K_2CaP_2O_7$ and $Ca_2P_2O_7$.

In a particularly preferred embodiment of the invention, some of the raw materials used can also be melted separately in order to obtain a glass which acts as a sintering aid and can be used for the production of the spongiosa-like bodies in a particularly advantageous manner. The aforesaid glass is ground and can be added to the slurry consisting of the material according to the invention which has been ground following the melting and cooling processes and then processed into a slurry. The glass melted separately can be added to the slurry in an amount ranging up to 15% by weight relative to the amount of solid matter contained therein, providing, however, that the individual components are not contained in the composition in larger amounts than those indicated in the invention. Such a glass can in particular be produced on the basis of $SiO_2$, $MgO$ and $Na_2O$.

In this embodiment, the sintering process leads to a very solid structure of the moulded body, whereas parts of the moulded body may crumble away if all components are melted together and then sintered. The glass melted separately has a grain size $D_{50}$ ranging between 0.7 and 7 μm when being added to the ground material, whose grain size is similar or larger.

Therefore the present invention also relates to a glass used as a sintering aid for resorbable materials comprising calcium phosphates with the exception of β-TCP, which glass is characterized by the following chemical composition in % by weight:

$SiO_2$: 73-78, preferably 74-75
$MgO$: 8-11, preferably 8.5-10
$Na_2O$: 12-19, preferably 14.5-17
$K_2O$: 0-22, preferably 0-5
$P_2O_5$: 0-20, preferably 0-10.

Another processing option consists in grinding the material, adding commonly used sintering aids and processing the slurry obtained in this way into a sheet which has an open-pore structure once the firing process is finished.

Advantageously, the material according to the invention can also be provided in combination with a metallic implant surface. The material's coefficient of expansion ranges between 10 and $17 \times 10^{-6} K^{-1}$, measured using a dilatometer (silica glass pushrod dilatometer (Kieselglas-Schubstangen-Dilatometer) manufactured by Netzsch Gerätebau GmbH, Germany), so that an adaption to known metals, e.g. chromium-cobalt-molybdenum steels having similar coefficients of expansion, is particular advantageous.

The present invention also relates to the use of the glassy-crystalline material according to the invention for manufacturing granulated materials, ceramic bodies or ceramic sheets.

The invention will hereinafter be explained by means of examples. All percentages are by weight unless indicated otherwise.

BRIEF DESCRIPTION OF THE DRAWINGS

FIG. 1: shows $^{31}$P-MAS-NMR spectra of the materials 50-25-25 and 30-50-20 according to the invention, whose composition corresponds to Example 2 and whose phases correspond to Example 5 (MAS—Magic Angle Spinning);

FIG. 2: shows the $^{31}$P-MAS-NMR spectrum of β-TCP.

DETAILED DESCRIPTION OF THE INVENTION

Example 1 (Comparative Example)

The following materials were synthesized according to the amounts indicated in the table in % by weight:

| Code | CaO | MgO | $P_2O_5$ | $Na_2O$ | $K_2O$ | $SiO_2$ |
|---|---|---|---|---|---|---|
| 100-0-0 | 30.67 | 2.45 | 43.14 | 9.42 | 14.32 | 0.00 |
| 97.5-0-2.5 | 29.92 | 2.39 | 44.53 | 9.19 | 13.97 | 0.00 |
| 95-0-5 | 29.21 | 2.33 | 45.85 | 8.97 | 13.64 | 0.00 |

The procedure for preparing the materials was as follows: The mixtures to be melted were weighed in as follows:

| Code | $CaCO_3$ In g | MgO in g | 85% $H_3PO_4$ in ml | $Na_2CO_3$ in g | $K_2CO_3$ in g | $SiO_2$ in g |
|---|---|---|---|---|---|---|
| 100-0-0 | 54.74 | 2.45 | 41.48 | 16.11 | 21.01 | 0 |
| 97.5-0-2.5 | 53.40 | 2.39 | 42.82 | 15.72 | 20.50 | 0 |
| 95-0-5 | 52.13 | 2.33 | 44.09 | 15.34 | 20.01 | 0 |

First, the components comprising calcium, magnesium, sodium and potassium and optionally silicon, are weighed in. Once the weighing-in process is finished, each mixture is mixed in a tumbling mixer for one hour. Then the 85% orthophosphoric acid is added to the mixture, the mixture is thoroughly ground in a mortar, stirred and dried at 100° C. for one hour, ground in a mortar again and stored once more in a drying chamber at 100° C. for one hour. Subsequently, the mixture was once again ground in a mortar, filled into a Pt/Rh crucible and heated up to 400° C., at which temperature it was held for one hour, then heated up to 800° C., at which temperature it was again held for one hour, and then heated up to 1,000° C., at which temperature it was also held for one hour. The sinter cake produced in this way was cooled in air and ground in a mortar again in order to make it more homogeneous. The pretreated mixture was then filled into a platinum crucible and heated up to 1,600° C. in a melting furnace. Once the aforesaid temperature had been reached, the melt was maintained at this temperature for half an hour. The low-viscosity, homogeneous melts were then poured onto a steel plate and pressed using a second steel plate so that a salt-like solidified plate was obtained. The crystallization taking place during this stage gives an opaque, white colour to the bodies obtained by the melting process.

X-ray measurements of the aforsaid samples showed that they contained $Ca_2K_{1-x}Na_{1+x}(PO_4)_2$ as main crystal phase, which is not included in the subject matter of the present invention but filed as patent application on the same day by the inventors. However, these examples can also be used to demonstrate the positive effect of diphosphate contents (cf. values in Example 5) with regard to solubility (cf. values in Example 4). A higher diphosphate content clearly increased solubility.

Example 2

Following the same production procedure as described in Example 1, i.e. preparing a mixture of calcium carbonate, sodium carbonate, potassium carbonate and orthophosphoric acid, the following compositions were synthesized according to the amounts indicated in the table in % by weight:

| Code | CaO | MgO | $P_2O_5$ | $Na_2O$ | $K_2O$ | $SiO_2$ |
|---|---|---|---|---|---|---|
| 50-25-25 | 39.86 | 1.25 | 46.82 | 4.79 | 7.28 | 0 |
| 60-20-20 | 37.99 | 1.49 | 46.08 | 5.73 | 8.71 | 0 |
| 40-30-30 | 41.74 | 1 | 47.58 | 3.84 | 5.84 | 0 |
| 80-10-10 | 34.31 | 1.97 | 44.6 | 7.59 | 11.53 | 0 |
| 60-30-10 | 39.05 | 1.48 | 45.13 | 5.69 | 8.65 | 0 |
| 50-40-10 | 41.43 | 1.23 | 45.39 | 4.74 | 7.21 | 0 |
| 50-32.5-17.5 | 40.65 | 1.24 | 46.1 | 4.77 | 7.24 | 0 |
| 40-50-10 | 43.8 | 0.99 | 45.65 | 3.79 | 5.77 | 0 |
| 40-40-20 | 42.78 | 0.99 | 46.61 | 3.82 | 5.8 | 0 |
| 30-50-20 | 45.16 | 0.75 | 46.88 | 2.86 | 4.35 | 0 |
| 20-50-30 | 46.55 | 0.5 | 48.11 | 1.92 | 2.92 | 0 |
| 30-0-70 | 40.1 | 0.73 | 52.04 | 2.83 | 4.3 | 0 |
| 50-0-50 | 37.4 | 1.23 | 49.5 | 4.71 | 7.16 | 0 |
| 70-0-30 | 34.71 | 1.72 | 46.96 | 6.59 | 10.02 | 0 |
| 50-40-10-Si | 41.4 | 1.3 | 44.4 | 10.2 | 1.7 | 1 |

Low-viscosity melts were obtained for all compositions, which melts spontaneously crystallized when being cooled. The crystallization products had a white colour.

Example 3

Another manufacturing option consists, inter alia, in that the amount of phosphorus or phosphate may be brought in by means of a calcium carrier, either in part or, as in the present example, in its entirety. The following composition was synthesized according to the amounts indicated in the table in % by weight:

| Code | CaO | MgO | $P_2O_5$ | $Na_2O$ | $K_2O$ | $SiO_2$ |
|---|---|---|---|---|---|---|
| 60-20-20 | 37.99 | 1.49 | 46.08 | 5.73 | 8.71 | 0 |

The mixture to be melted was weighed in as follows:

| Code | $CaCO_3$ in g | MgO in g | 85% $H_3PO_4$ in ml | $Na_2CO_3$ in g | $K_2CO_3$ in g | $CaHPO_4$ in g |
|---|---|---|---|---|---|---|
| 60-20-20 | 2.82 | 1.49 | 0.00 | 9.80 | 12.78 | 88.34 |

The mixture to be melted was weighed in according to the amounts indicated above, mixed in a tumbling mixer for one hour, filled into a platinum crucible, placed in a furnace which had been preheated to 400° C. and held at this temperature for 16 hours. The crucible was taken out and the furnace was preheated to 600° C., which temperature was maintained for 4 hours, and the furnace was then preheated to 950° C. The crucible was then held in the furnace preheated to 950° C. for 6 hours. Subsequently, the sample was heated up to 1,600° C. and held at this temperature for half an hour. The low-viscosity, homogeneous melt was then poured onto a steel plate and pressed using a second steel plate so that a salt-like solidified plate was obtained. The crystallization taking place during this stage gives an opaque, white colour to the bodies obtained by the melting process. A discoloration can be observed, depending upon the $CaHPO_4$ component used and undesirable amounts of iron and/or manganese contained therein.

It is also possible to directly quench the melt in a water bath once the melting process (1,600° C., 0.5 h) is finished (fritting) in order to facilitate the further comminution of the product obtained by the melting process if it is to be further processed in the form of a slurry.

Example 4

The samples according to Example 1 and selected samples according to Example 2 (see the following table) were used to produce granulated materials having a grain size ranging between 315 μm and 400 μm in order to determine solubility. The solvent used was 0,2M TRIS-HCl buffer solution with a pH value of 7.4 and at a temperature of 37° C. The analyzed amount was 50 mg using 40 ml solvent. The granulated materials were stored at 37° C. for a period of 120 h. Subsequently, the total solubility was determined by determining the individual ions (of Ca, Mg, P, Na, K) in the solution by means of an ICP measurement:

| Code | Solubility [μg/mg] |
|---|---|
| 50-25-25 | 187 ± 10 |
| 60-20-20 | 164 ± 14 |
| 40-30-30 | 160 ± 15 |
| 80-10-10 | 108 ± 8 |
| 60-30-10 | 123 ± 11 |
| 50-40-10 | 123 ± 7 |
| 50-32.5-17.5 | 127 ± 22 |
| 40-50-10 | 105 ± 16 |
| 40-40-20 | 152 ± 4 |
| 30-50-20 | 121 ± 14 |
| 20-50-30 | 78 ± 4 |
| 100-0-0 | 95 ± 8 |
| 97.5-0-2.5 | 134 ± 16 |
| 95-0-5 | 221 ± 22 |

Surprisingly, the compositions according to Example 2 have impressively high solubility values compared to the compositions according to Example 1 although the sum of the alkaline constituents, i.e. relative to sodium oxide and potassium oxide, is much smaller in the compositions according to Example 2.

Example 5

$^{31}$P-MAS-NMR spectra of the samples according to Example 1 and selected samples according to Example 2 were recorded with a waiting time of 120 s between the individual pulses. The samples rotated at a speed of 12.5 kHz.

The quantitative composition of the samples as regards their phosphate content is indicated in the following table:

| Code | Orthophosphate content [(PO$_4$)$^{3-}$] in % | Diphosphate content [(P$_2$O$_7$)$^{2-}$] in % | Chain phosphate content [predominantly (PO$_3$)$^{1-}$ in %] |
|---|---|---|---|
| 50-40-10 | 92.5 | 7.5 | — |
| 50-32.5-17 | 93 | 7 | — |
| 50-25-25 | 86 | 14 | — |
| 40-50-10 | 91 | 9 | — |
| 40-40-20 | 84 | 16 | — |
| 40-30-30 | 82.5 | 13 | 4.5 |
| 30-50-20 | 88 | 9 | 3 |
| 20-50-30 | 73 | 27 | — |
| 60-20-20 | 92 | 8 | — |
| 100-0-0 | 99.5-96 | 0.5-4 | — |
| 97.5-0-2.5 | 88 | 12 | — |
| 95-0-5 | 79 | 21 | — |

The range indicated for the composition 100-0-0 is based on the analysis of three batches one of which was synthesized according to the manufacturing method described in Example 3, whereas only one sample was analysed for each of the other compositions.

Example 6

In the zirconium oxide bowl (250 ml) of a planetary mill, the products obtained by the melting process having a composition according to codes 30-50-20, 40-30-30 and 60-20-20 and a composition GB9/1 according to Biomaterials 16 (1995)1241-1248 were ground under the same conditions (two times for 20 min). The results are shown in the following table according to which the compositions according to the invention yield smaller grain size fractions under the same grinding conditions:

| Code | D$_{50}$ value [in µm] |
|---|---|
| 30-50-20 | 4.21 |
| 40-30-30 | 3.98 |
| 60-20-20 | 3.67 |
| GB9/1 | 6.50 |

Example 7

The ground 30-50-20 sample according to Example 6 is to be processed into "scaffolds". For this purpose, a slurry was produced by combining 100 g of the ground material with 45 g of a mixture consisting of 90% polyethylene glycol and 10% of a commercially available surface-active agent and adding 5 ml isopropyl alcohol. The slurry obtained in this way is applied onto open-pore PUR sponges whose porosity ranges between 80 and 20 ppi (pores per inch) by repeatedly immersing and squeezing the sponges, dried overnight in a drying chamber at 120° C. and then slowly heated up to 1,000° C. at a rate of 10° C. per minute. The result is a spongiosa-like material the structure of which resembles that of the sponge used, while the PUR sponge has burnt completely.

Example 8

The ground 60-20-20 sample according to Example 6 is to be processed into "scaffolds". This was done according to the method described in Example 7. The result was not completely satisfying as the sample obtained in Example 7 obviously had a more solid structure. In order to compensate for this deficiency, 3% by weight of a previously produced glass having a chemical composition of (in % by weight) 74.97 SiO$_2$, 9.22 MgO and 15.81 Na$_2$O (melted as 27.04 Na$_2$CO$_3$) and a D$_{50}$ value of 6.56 µm was added to the ground material according to 60-20-20 as a sintering aid. Then a slurry was produced by combining 100 g of this powder mixture with 45 g of a mixture consisting of 90% polyethylene glycol and 10% of a commercially available surface-active agent and adding 5 ml isopropyl alcohol. The slurry obtained in this way is applied onto open-pore PUR sponges whose porosity ranges between 80 and 20 ppi (pores per inch) by repeatedly immersing and squeezing the sponges, dried overnight in a drying chamber at 120° C. and then slowly heated up to 1,000° C. at a rate of 10° C. per minute. The result is a spongiosa-like material the structure of which resembles that of the sponge used, while the PUR sponge has burnt completely.

Example 9

Samples were prepared according to Example 2 and selected samples thereof were analysed using $^{31}$P-NMR measurements. The $^{31}$P-MAS-NMR spectra were recorded with a waiting time of 120 s between the individual pulses. The samples rotated at a speed of 12.5 kHz.

As a result, it can be shown that the samples according to the invention, e.g. the 50-25-25 and 30-50-20 samples (cf. FIG. 1), in their majority do not contain β-TCP unlike a certified reference sample consisting of β-TCP (Clarkson Chromatography Products, Inc., South Williamsport, Pa., USA) (cf. FIG. 2), but can be allocated to the Ca$_{10}$Na(PO$_4$)$_7$ or Ca$_{10}$K(PO$_4$)$_7$ crystal phases according to the invention. It cannot be ruled out, but is rather probable instead, that possibly there are also mixed crystal phases in between the two crystal phases Ca$_{10}$Na(PO$_4$)$_7$ and Ca$_{10}$K(PO$_4$)$_7$. This is a scientific problem to be clarified in the future and has no influence whatsoever on the manufacture and use of the material according to the invention.

In FIG. 1, the left peak indicates Q$_0$-groups and the right, higher peak Q$_1$-groups.

The main phases according to the invention, i.e. Ca$_{10}$Na (PO$_4$)$_7$ or Ca$_{10}$K(PO$_4$)$_7$ or Na-K ratios in between, could be clearly identified detecting Q$_0$-groups by means of NMR analyses. A clear allocation was possible even in those cases in which Ca$_{10}$Na(PO$_4$)$_7$ or Ca$_{10}$K(PO$_4$)$_7$ make up the main phases and β-TCP occurs as a constituent of a secondary phase.

Example 10

Material composed according to code 30-50-20 was freshly ground, 1 g of a grain size fraction <45 µm was added into 100 ml E-pure water, and the pH value was determined after 1 min and after 72 h. The result was 9.71 after one minute and 8.3 after 72 hours, i.e. a clear change towards physiological conditions could be observed.

Example 11

In order to enhance this effect a priori, the following experiment was carried out: A spongiosa-like body was produced according to Example 7, i.e. the composition according to code 30-50-20 was applied onto a PUR sponge and sintered, except that the sponge used in the present example had a porosity of 45 ppi.

The moulded body obtained in this way, whose outer dimensions were approx. 12 mm×10 mm×6 mm, was immersed in 100 ml E-pure water and the pH value was measured after 10 min. The measured value was 8.25.

Subsequently, the moulded body was eluted in E-pure water at 60° C. and a pressure of 3 bars for one hour. The moulded body was then rinsed 5 times in 20 ml fresh E-pure water, immersed in 100 ml E-pure water again, and pH values of 7.84 and 7.86 were measured after 1 hour and 4 hours respectively.

This demonstrates that the pretreatment of spongiosa-like bodies described above is a useful activity as products pretreated in this way have a lower basicity, which can be advantageous both for implantation in vivo and for tissue engineering ex vivo or in vitro.

Example 12

An important feature with regard to the coating of materials with the resorbable materials according to the invention consists in that the thermal coefficient of expansion can be varied, bearing in mind e.g. that this coefficient is approx. $8 \cdot 10^{-6} K^{-1}$ for titanium implants and approx. $14\text{-}16 \cdot 10^{-6} K^{-1}$ for Co-Cr-Mo steels (depending upon the constituents of the alloy). In order to obtain a composite material which is optimally suited to its intended use, the temperature range in which the material is applied onto the metallic substrate must be carefully selected as in this way the substrate can be subjected to compressive strain in a targeted manner during the coating process thus obtaining a composite material which in general is regarded as mechanically more stable.

The following table shows some of the possible variations:

| Sample | $CE_{30\text{-}100}$ $(10^{-6} K^{-1})$ | $CE_{30\text{-}200}$ $(10^{-6} K^{-1})$ | $CE_{30\text{-}300}$ $(10^{-6} K^{-1})$ |
|---|---|---|---|
| 40-30-30 | 13.45 | 14.85 | 16.35 |
| 60-20-20 | 11.09 | 12.32 | 13.43 |
| 40-40-20 | 13.24 | 14.04 | 14.95 |
| 30-50-20 | 12.12 | 13.14 | 14.46 |
| 50-25-25 | 12.22 | 12.65 | 14.14 |

In the table, $CE_{30\text{-}100}$ is the coefficient of expansion between 30 and 100° C., $CE_{30\text{-}200}$ is the coefficient of expansion between 30 and 200° C., and $CE_{30\text{-}300}$ is the coefficient of expansion between 30 and 300° C.

The invention claimed is:

1. A bone replacement material with orthophosphate, wherein
   a) according to $^{31}P$-NMR measurements, said bone replacement material comprises $Q_0$-groups of orthophosphate and $Q_1$-groups of diphosphate, the orthophosphates or $Q_0$-groups making up 65 to 99.9% by weight relative to the total phosphorus content of the finished material and the diphosphates or $Q_1$-groups making up 0.1 to 35% by weight relative to the total phosphorus content of the finished material, and
   b) according to X-ray diffractometric measurements and relative to the total weight of the finished material, 35 to 99.9% by weight of a main crystal phase consisting of $Ca_{10}Na(PO_4)_7$, $Ca_{10}K(PO_4)_7$, mixtures thereof or mixed crystals according to the general formula $Ca_{10}K_xNa_{1-x}(PO_4)_7$, where x=0 to 1, is contained in the bone replacement material and 0.1 to 25% by weight of a substance selected from the group consisting of $Na_2CaP_2O_7$, $K_2CaP_2O_7$, $Ca_2P_2O_7$ and mixtures thereof is contained as a secondary crystal phase, and
   c) the X-ray amorphous phases contained besides the main crystal phase jointly make up 0.1 to 65% by weight relative to the total weight of the finished material.

2. A bone replacement material with orthophosphate, wherein
   ) according to $^{31}P$-NMR measurements, the bone replacement material comprises $Q_0$-groups of orthophosphate and $Q_1$-groups of diphosphate, the orthophosphates or $Q_0$-groups making up 65 to 99.9% by weight relative to the total phosphorus content of the finished material and the diphosphates or $Q_1$-groups making up 0.1 to 35% by weight relative to the total phosphorus content of the finished material, and
   b) according to X-ray diffractometric measurements and relative to the total weight of the finished material, 35 to 99.9% by weight of a main crystal phase consisting of $Ca_{10}Na(PO_4)_7$, $Ca_{10}K(PO_4)_7$, mixtures thereof or mixed crystals according to the general formula $Ca_{10}K_xNa_{1-x}(PO_4)_7$, where x=0 to 1, is contained in the bone replacement material and 0.1 to 25% by weight of a substance selected from the group consisting of $Na_2CaP_2O_7$, $K_2CaP_2O_7$, $Ca_2P_2O_7$ and mixtures thereof is contained as a secondary crystal phase, and
   c) the X-ray amorphous phases contained besides the main crystal phase jointly make up 0.1 to 65% by weight relative to the total weight of the finished material,
   obtainable by
   mixing raw materials containing (in % by weight) 34-48 CaO, 1.5-10.5 $Na_2O$, 1-11 $K_2O$, 1.5-3 MgO and 0.1-4 $SiO_2$ and treating the aforesaid mixture with $H_3PO_4$ in an amount corresponding to 44-54 $P_2O_5$, $SiO_2$ or MgO or a mixture thereof making up at least 1% by weight, homogenizing and drying the mixture and subjecting it to a step-by-step thermal treatment lasting 1-2h at 350-450° C., 750-850° C. and 950-1,050° C. respectively, melting the mixture at between 1,550 and 1,6500C, holding it at the melting temperature for between 10 and 60 minutes and finally cooling the mixture in a spontaneous or temperature-controlled manner, grinding it, if necessary, and sintering it to obtain moulded bodies.

3. A bone replacement material according to claim 1, wherein in addition one or more chain phosphates from the group consisting of $NaPO_3$, $KPO_3$ and mixed crystals thereof are contained, which chain phosphates are detectable as $Q_2$-groups according to $^{31}P$-NMR measurements, or the orthophosphate β-tricalcium phosphate, which can be detected as $Q_0$-groups according to $_{31}P$-NMR measurements, or mixtures thereof are contained.

4. A bone replacement material according to claim 2, wherein the chain phosphates make up 0.5 to 10% by weight.

5. A bone replacement material according to claim 2, wherein the secondary crystal phase contains a silicate phase corresponding to the $SiO_2$ content.

6. A bone replacement material according to claim 1, wherein the crystalline, amorphous or both phases contain magnesium in an amount ranging up to 10% by weight, calculated as MgO and relative to the weight of the finished material.

7. A bone replacement material according to claim 1, wherein the orthophosphates makes up 40 to 95% by weight.

8. A bone replacement material according to claim 7, wherein the orthophosphates makes up 50 to 90% by weight.

9. A bone replacement material according to claim 1, wherein the diphosphate phase makes up 1 to 22% by weight.

10. A bone replacement material according to claim 9, wherein the diphosphate phase makes up 5 to 8% by weight.

11. A bone replacement material according to claim 1, wherein the secondary crystal phase makes up 0.1 to 25% by weight.

12. A bone replacement material according to claim 11, wherein the secondary crystal phase makes up 1 to 25% by weight.

13. A bone replacement material according to claim 1, wherein the total solubility ranges between 60 and 250 µg/mg relative to the starting material if the test is carried out in 0.2M TRLS-HCl buffer solution at pH 7.4, T =37° C. using a grain size fraction of 315-400 µm, the duration of the test being 120 h and the ratio of weighed-in sample to buffer solution being 50mg to 40ml.

14. A bone replacement material according to claim 1, wherein the coefficient of expansion ranges between 10 and $17 \times 10^{-6}$ $K^{-1}$, measured using a dilatometer.

15. A bone replacement material according to claim 1, wherein the pH value of the surface changes by at least 0.3 units, towards the neutral point within the alkaline range if the material is stored in deionized water at room temperature for 72 hours or heated up to 60° C. for 1 hour at a pressure of 1-3 bars and rinsed with deoinized water.

16. A bone replacement material according to claim 1, wherein said material is provided in combination with a metallic implant surface.

17. A bone replacement material according to claim 1, wherein said material is provided in the form of granulated materials, ceramic bodies or ceramic sheets.

18. The bone replacement material according to claim 1, wherein x ranges between 0.1 and 1.

* * * * *